United States Patent [19]

Noyori et al.

[11] Patent Number: 4,851,537
[45] Date of Patent: Jul. 25, 1989

[54] PROCESS FOR PREPARING N-ACYLTETRAHYDROISOQUINOLINE

[75] Inventors: Ryoji Noyori; Masato Kitamura; Hidemasa Takaya, all of Aichi; Hidenori Kumobayashi; Susumu Akutagawa, both of Kanagawa, all of Japan

[73] Assignee: Takasago Perfumery Co., Ltd., Tokyo, Japan

[21] Appl. No.: 38,571

[22] Filed: Apr. 15, 1987

[30] Foreign Application Priority Data

May 13, 1986 [JP] Japan ................ 61-108889

[51] Int. Cl.⁴ .................................. C07D 217/16
[52] U.S. Cl. ...................................... 546/146
[58] Field of Search ............................ 546/146

[56] References Cited

FOREIGN PATENT DOCUMENTS 0174057 3/1986 European Pat. Off. .

OTHER PUBLICATIONS

Lenz, et al., "Chemical Abstracts", vol. 86, 1977, col. 86:155842a.
Achiwa, "Chemical Abstracts", vol. 88, 1978, col. 88:105618c.
Achiwa, "Chemical Abstracts", vol. 90, 1979, col. 90:86122j.
Hara, et al., "Chemical Absracts", vol. 93, 1980, col. 93:239718x.
Noyori, et al., "Chemical Abstracts", vol. 105, 1986, col. 105:19145a.
T. Shono et al., Tetrahedron Letters, vol. 22, #25, pp. 2385-2388 (1981).
H. Kagan et al., J. or Organometallic Chem., vol. 90, pp. 353-365 (1975).
A. Meyers et al., J. Am. Chem. Soc., vol. 105, pp. 117-118 (1983).
S. Yamada et al., Tetrahedron Letters, No. 22, pp. 2215-2218 (1972).
W. Awe et al., Berichte Der Deutschen Chem. Gesell., vol. 70, pp. 472-478 (1937).

T. Ikariya et al., J. Chem. Soc. Chem. Comm., pp. 922-924 (1985).

Primary Examiner—Glennon H. Hollrah
Assistant Examiner—James H. Turnipseed
Attorney, Agent, or Firm—Sughrue, Mion, Zinn, Macpeak & Seas

[57] ABSTRACT

A process for preparing an N-acyltetrahydroisoquinoline represented by formula (II)

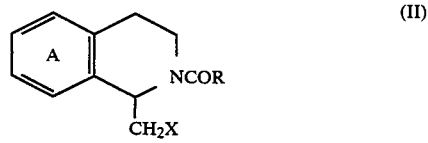

wherein A represents a phenylene ring substituted with a hydroxyl group, a lower alkoxy group, an acetoxy group, or a benzyloxy group; R represents a hydrogen atom, a lower alkyl group, or a phenyl group; and X represents a hydrogen atoms, a phenyl group, or a phenyl group substituted with a hydroxyl group, a lower alkoxy group, or an acetoxy group, which comprises asymmetrically hydrogenating an N-acyl-1-methylenetetrahydroisoquinoline or N-acyl-1-benzylidenetetrahydroisoquinoline represented by formula (I)

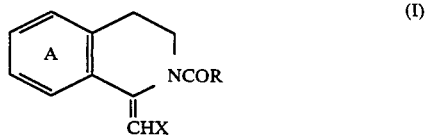

wherein A, R, and X are as defined above, in the presence of an optically active ruthenium-phosphine complex as a catalyst. The process exclusively and efficiently provides a useful isomer of the N-acyltetrahydroisoquinoline of high purity which is useful as an intermediate for synthesizing isoquinoline type alkaloids as pharmaceuticals without involving optical resolution of a racemate.

6 Claims, No Drawings

PROCESS FOR PREPARING N-ACYLTETRAHYDROISOQUINOLINE

FIELD OF THE INVENTION

This invention relates to a process for efficiently and exclusively preparing interesting optical isomers of various tetrahydroisoquinolines that are useful as intermediates for synthesizing isoquinoline type alkaloids as pharmaceuticals, etc.

BACKGROUND OF THE INVENTION

Physiologically active organic compounds have greatly varying physiological activities depending on their optical isomers. In some cases, they exhibit activities entirely opposite to expectation. Therefore, it is an important subject to efficiently and exclusively synthesize only useful optical isomers.

Isoquinoline type alkaloids are a series of physiologically active substances obtained from naturally-occurring materials and are widely employed as pharmaceuticals. In particular, benzylisoquinoline type compounds are not only important per se but also useful as intermediates for introducing into various other physiologically active substances such as morphine. Several processes are known for obtaining the benzylisoquinoline type compounds as optically active isomers. For example, tetrahydropapaverine is synthesized by forming its racemate, for example, by reduction of papaverine as described in, e.g., W. Awe et al., *Ber.* 70, 472 (1937) or addition of a benzyl group to tetrahydroisoquinoline as described, e.g., in T. Shono et al., *Tetrahedron Letter*, Vol. 22, No. 25, 2385 (1981) and then optically resolving the racemate. Such a process involving optical resolution of a racemate is uneconomical because an enantiomer having a configuration which is a mirror image of the desired optical isomer is discarded as unnecessary.

In recent years, many attempts have been directed to asymmetric syntheses. Proposals for asymmetric synthesis include, for example, asymmetric reduction of 3,4-dihydropapaverine as reported in H. B. Kagan et al., *J. Organomet. Chem.*, Vol. 90, 353 (1975), asymmetric alkylation to tetrahydroisoquinoline as reported in A. I. Meyer et al., *J. Am. Chem. Soc.*, Vol. 105, 117 (1983), and biosynthesis starting with an amino acid as reported in S. Yamada et al., *Tetrahedron Letter*, No. 22, 2215 (1972). However, any of these processes involve complicated steps and are not satisfactory for the production on an industrial scale.

Accordingly, it has been keenly demanded to establish a process which does not require complicated operations and directly provides an optical isomer of interest with high efficiency.

SUMMARY OF THE INVENTION

The inventors have conducted extensive investigations on processes for efficiently obtaining optically active benzylisoquinolines which are key compounds for syntheses of various isoquinoline type alkaloids. As a result, it has now been found that benzylisoquinolines having an optical purity of approximately 100% can be obtained by asymmetrically hydrogenating a double bond of methylene type isoquinolines or benzylidene type isoquinolines in the presence of a ruthenium-phosphine complex as a catalyst.

The present invention relates to a process for preparing an N-acyltetrahydroisoquinoline represented by formula (II)

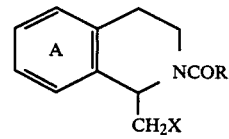

wherein A represents a phenylene ring substituted with a hydroxyl group, a lower alkoxy group (e.g., those having from 1 to 4 carbon atoms), an acetoxy group, or a benzyloxy group; R represents a hydrogen atom, a lower alkyl group (e.g., those having from 1 to 4 carbon atoms), or a phenyl group; and X represents a hydrogen atom, a phenyl group, or a phenyl group substituted with a hydroxyl group, a lower alkoxy group (e.g., those having from 1 to 4 carbon atoms), or an acetoxy group, which comprises asymmetrically hydrogenating an N-acyl-1-methylenetetrahydroisoquinoline or N-acyl-1-benzylidenetetrahydroisoquinoline represented by formula (I)

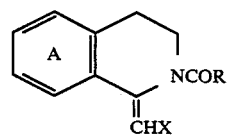

wherein A, R, and X are as defined above, in the presence of an optically active ruthenium-phosphine complex as a catalyst.

DETAILED DESCRIPTION OF THE INVENTION

In carrying out the process according to the present invention, the substrate represented by formula (I) is disclosed in a solvent such as methylene chloride, and an additional solvent such as methanol or ethanol is then added thereto to prepare a substrate solution. Separately, a solution of a ruthenium-phosphine complex as hereinafter described is prepared in the same manner as described above. Both the solutions are mixed, and the mixture is transferred to an autoclave. Hydrogen is then introduced to the mixture, and the reaction is carried out under a hydrogen pressure of from 1 to 10 kg/cm$^2$ at a temperature of from 10° to 40° C. for a period of from 10 to 160 hours. These reaction conditions can be decided appropriately depending on the kinds of the substrate and catalyst used. After completion of the reaction, the solvent is removed by distillation, and the residue is purified in a known manner such as silica gel column chromatography to thereby obtain an N-acyltetrahydroisoquinoline of formula (II) in a yield of from 80 to 100%. When a diastereomer which is obtained by deacylating the resulting product and then reacting the product with 2,3,4,6-tetra-O-acetyl-β-D-glycopyranosyl isothiocyanate is analyzed by high performance liquid chromatography, it is proved that the above obtained hydrogenation product has an optical purity ranging from 95 to 99.5%ee.

Typical examples of the compounds of formula (I) include:

(1)  (Z)-N-Acetyl-6,7-dimethoxy-1-(3,4-dimethoxyphenylmethylene)-1,2,3,4-tetrahydroisoquinoline (This compound gives tetrahydropapaverine through asymmetric hydrogenation according to the process of the invention, followed by deacetylation.)

(2) (Z)-N-Benzoyl-6,7-dimethoxy-1-(3,4-dimethoxyphenylmethylene)-1,2,3,4-tetrahydroisoquinoline (This compound gives tetrahydropapaverine through the same steps as above.)

(3) (Z)-N-Formyl-6,7-dimethoxy-1-(3,4-dimethoxyphenylmethylene)-1,2,3,4-tetrahydroisoquinoline (This compound gives tetrahydropapaverine through the same steps as above.)

(4) (Z)-N-Acetyl-6,7-dimethoxy-1-methylene-1,2,3,4-tetrahydroisoquinoline (This compound gives Salsolidine through the same steps as above.)

(5) (Z)-N-Acetyl-7-acetoxy-1-(3-acetoxy-4-methoxyphenylmethylene)-6-methoxy-1,2,3,4-tetrahydroisoquinoline (This compound gives Norreticurine through the same step as above.)

(6) (Z)-N-Acetyl-6,7-dibenzyloxy-1-(3,4,5-trimethoxyphenylmethylene)-1,2,3,4-tetrahydroisoquinoline (This compound gives Tretoquinol through asymmetric hydrogenation according to the process of the invention, followed by deacetylation and debenzoylation.)

The optically active ruthenium-phosphine complex which can be used as a catalyst in the process of this invention includes those in which 2,2'-bis(diphenylphosphino)-1,1'-binaphthyl (hereinafter referred to as BINAP), etc. is coordinated to metallic ruthenium as disclosed in T. Ikariya et al., *J. Chem. Soc., Chem. Commun.*, pp. 922 (1985) and Japanese Patent Application (OPI) No. 63690/86 (corresponding to European Pat. No. 174,057A) (the term "OPI" as used herein means "unexamined published application"). Typical examples of these complexes include:

(1) $Ru_2Cl_4(BINAP)_2N(C_2H_5)_3$ (2) $Ru_2Cl_4(p\text{-}Tol\ BINAP)_2N(C_2H_5)_3$ (wherein p-Tol BINAP represents 2,2'-bis(di-p-tolylphosphino)-1,1'-binaphthyl)

(3) $RuHCl(BINAP)_2$ (4) $Ru_2Cl_4(p\text{-}t\text{-}Bu\ BINAP)_2N(C_2H_5)_3$ (wherein p-t-Bu BINAP represents 2,2'-bis(di-p-t-butylphenylphosphino)-1,1'-binaphthyl)

(5) $Ru_2Cl_4(5\text{-acetylamino\ BINAP})_2N(C_2H_5)_3$ (wherein 5-acetylamino BINAP represents 2,2'-bis(diphenylphosphino)-5,5'-diacetylamino-1,1'-binaphthyl)

In addition, ruthenium-phosphine complexes in which carboxyl groups are bonded to metallic ruthenium as represented by formula (III) shown below can also be used as a catalyst in the present invention.

Formula (III) is represented by

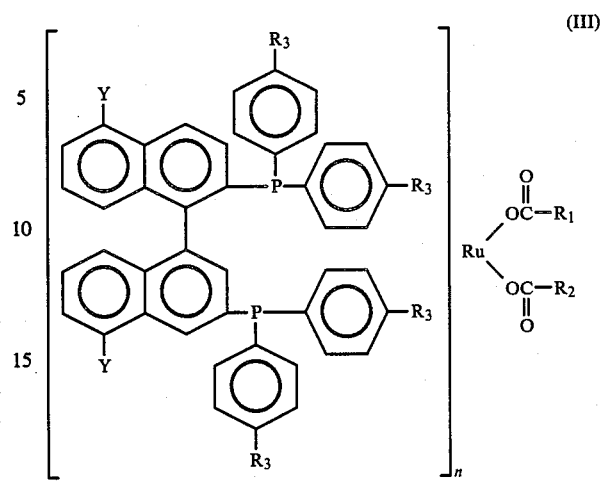

wherein Y represents a hydrogen atom, an amino group, an acetylamino group, or a sulfo group; $R_3$ represents a hydrogen atom or a lower alkyl group (e.g., those having from 1 to 4 carbon atoms); $R_1$ and $R_2$ each represents an alkyl group (e.g., those having from 1 to 9 carbon atoms), a halogenated lower alkyl group (e.g., those having from 1 to 4 carbon atoms; examples of the halogen include fluorine, chlorine, and bromine), a phenyl group, a phenyl group substituted with a lower alkyl group (e.g., those having from 1 to 4 carbon atoms), an α-aminoalkyl group (e.g., those having from 1 to 4 carbon atoms), or an α-aminophenylalkyl group (e.g., those having from 7 to 10 carbon atoms), or $R_1$ and $R_2$ are taken together to form an alkylene group (e.g., those having from 1 to 4 carbon atoms); and n represents 1 or 2.

Typical examples of the complex of formula (III) include:

(1) $Ru(BINAP)(O_2CCH_3)_2$ (2) $Ru(p\text{-}Tol\ BINAP)_2(O_2CCH_3)_2$ (3) $Ru(BINAP)(O_2Ct\text{-}Bu)_2$ (wherein t-Bu represents a t-butyl group)

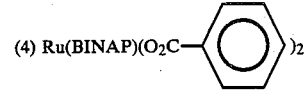

(5) $Ru(p\text{-}Tol\ BINAP)(O_2CCH_3)_2$
(6) $Ru(p\text{-}Tol\ BINAP)(O_2CCF_3)_2$
(7) $Ru(p\text{-}t\text{-}Bu\ BINAP)(O_2CCH_3)_2$
(8) $Ru(5\text{-acetylamino\ BINAP})(O_2CCH_3)_2$

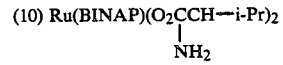

(wherein i-Pr represents an isopropyl group)

These ruthenium-phosphine complexes having carboxyl groups bonded to metallic ruthenium can be prepared from complexes obtainable by the process disclosed in Japanese Patent Application (OPI) No. 63690/86. For example, the complex of formula (III)

can be prepared by reacting Ru$_2$Cl$_4$(BINAP)$_2$N(C$_2$H$_5$)$_3$ with a carboxylic acid salt in an alcohol solvent such as t-butanol by heat-refluxing for about 12 hours, removing the solvent by distillation, and extracting the residue with a solvent such as diethyl ether or ethanol, followed by evaporation to dryness. Any desired carboxyl group can be introduced to the ruthenium atom by selecting the starting carboxylic acid to be used. For example, from the abovedescribed starting complex and sodium acetate is obtained Ru(BINAP)(O$_2$CCH$_3$)$_2$ of formula (III). The complex of formula (III) where trifluoroacetyl groups are bonded to ruthenium can be obtained by reacting the above prepared diacetate complex with trifluoroacetic acid in methylene chloride as a solvent at about 25° C. for about 12 hours. Further, the complex of formula (III) where a 2-equivalent ligand is coordinated to ruthenium can be prepared by reacting a complex of such a type, e.g., RuHCl(BINAP)$_2$, obtained by the process of Japanese Patent Application (OPI) No. 63690/86 with a carboxylic acid salt in a solvent such as methylene chloride.

The present invention will now be illustrated in greater detail with reference to the following examples, but it should be understood that the present invention is not limited thereto. In these examples, all the percents are by weight unless otherwise indicated.

EXAMPLE 1

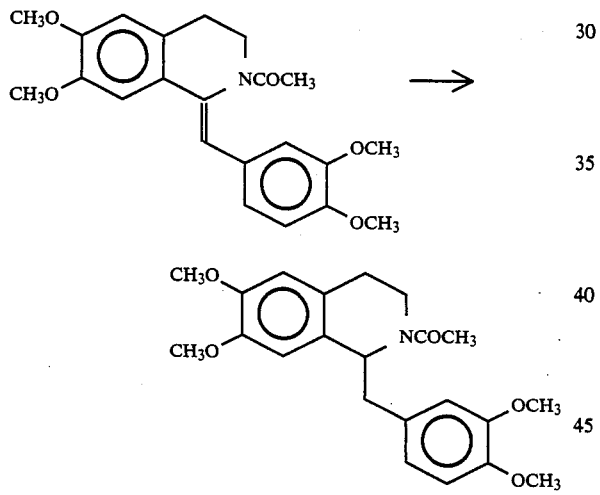

In a dried Schlenk-tube having its atmosphere displaced with argon, 205.9 mg (0.538 mmol) of (Z)-N-acetyl-6,7-dimethoxy-1-(3,4-dimethoxyphenylmethylene)-1,2,3,4-tetrahydroisoquinoline was charged and dissolved in 1.5 ml of methylene chloride. To the solution was further added 7.5 ml of ethanol. The resulting solution was frozen with liquid nitrogen three times for degasification in vacuo. Separately, in a dried Schlenk-tube having its atmosphere displaced with argon, 13.0 mg (7.8×10$^{-3}$ mmol) of Ru$_2$Cl$_4$((R)-(+)-BINAP)$_2$N(C$_2$H$_5$)$_3$ was charged and dissolved in 1.5 ml of methylene chloride which had been previously degassed by freezing three times. To the solution was further added 7.5 ml of ethanol. Both the solutions were mixed, and the mixture was transferred to an autoclave and stirred at 23° C. for 40 hours under a hydrogen pressure of 4 kg/cm$^2$. After completion of the reaction, the solvent was removed by distillation under reduced pressure, and the residue was purified by silica gel column chromatography (silica gel: 20 g, eluent: gel acetate/hexane=3:1 by volume) to obtain 202.5 mg (0.526 mmol) of white needle-like crystals (yield: 98%). The optical rotation [α]$_D^{24}$ was −91.2° (c=1.09, CHCl$_3$). The optical purity was found to be 99.5% as determined by the method hereinafter described (see Example 3).

$^1$H NMR (400 MHz, CDCl$_3$) δ ppm: 1.64 (1.2H, s), 2.14 (1.8H, s)(COCH$_3$), 2.6–3.2 (5.5H, m), 3.4–3.5 (0.5H, m)(—CH$_2$—), 3.63, 3.77, 3.84, 3.85, 3.86, 3.87 (six singlets, —OCH$_3$), 4.7–4.8 (0.7H, m), 5.6–5.7 (0.3H, m)(—CH=), 6.21 (0.5H, s), 6.5–6.8 (5H, m)(aromatic hydrogen).

EXAMPLE 2

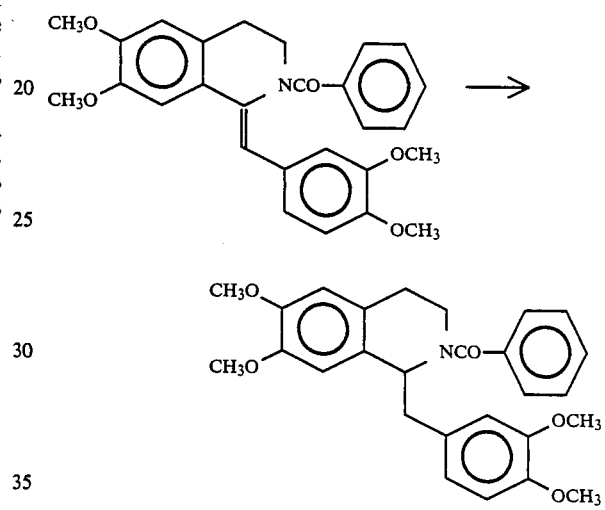

In a dried Schlenk-tube having its atmosphere displaced with argon, 188.2 mg (0.423 mmol) of (Z)-N-benzoyl-6,7-dimethoxy-1-(3,4-dimethoxyphenylmethylene)-1,2,3,4-tetrahydroisoquinoline was charged and dissolved in 4.5 ml of methylene chloride. To the solution was further added 7.5 ml of ethanol, followed by degasification by freezing three times. Separately, 5.0 mg (2.9×10$^{-3}$ mmol) of Ru$_2$Cl$_4$((R)-(+)-BINAP)$_2$N(C$_2$H$_5$)$_3$ as a catalyst was charged in a dried Schlenk-tube having its atmosphere displaced with argon and dissolved in 1.5 ml of methylene chloride. To the solution was further added 7.5 ml of ethanol. Both the solutions were mixed and subjected to hydrogenation in an autoclave at 23° C. for 160 hours under a hydrogen pressure of 4 kg/cm$^2$ while stirring. After completion of the reaction, the solvent was removed by distillation under reduced pressure, and the residue was purified by silica gel column chromatography (silica gel: 20 g, eluent: ethyl acetate/hexane=2:1 by volume) to obtain 189 mg (0.423 mmol) of pale yellow rod-like crystals in a yield of 100%.

[α]$_D^{24}$ −83.3° (c=1.13, CHCl$_3$).

The $^1$H NMR spectrum of this compound was consistent with that of benzoylated tetrahydropapaverine.

The optical purity of this compound was found to be 96.2%ee as determined by the method described in Example 3.

EXAMPLE 3

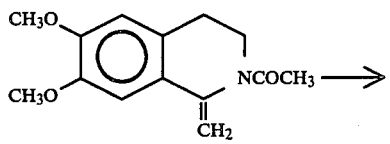

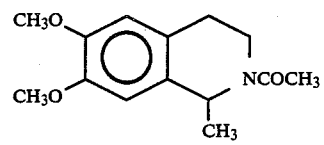

The same procedure of Example 2 was repeated except for using 67 mg (0.27 mmol) of N-acetyl-6,7-dimethoxy-1-methylene-1,2,3,4-tetrahydroisoquinoline to obtain 66 mg (0.265 mmol) of N-acetylsalsolidine in a yield of 97.7%.

The resulting N-acetylsalsolidine was mixed with 500 mg (7.58 mmol) of 85% potassium hydroxide, 0.2 ml (3.30 mmol) of 80% hydrazine hydrate, and 10 ml of ethylene glycol, and the mixture was allowed to react at 180° C. for 14 hours in an argon stream. After completion of the reaction, 30 ml of 1N hydrochloric acid was added to the reaction mixture, and the mixture was washed three times with 10 ml portions of methylene chloride. The aqueous layer was made alkaline by the addition of 30 ml of a 2N sodium hydroxide aqueous solution. The aqueous solution was extracted three times with 15 ml portions of methylene chloride. The extract was dried over anhydrous sodium sulfate, followed by distillation under reduced pressure to remove the methylene chloride to obtain 55 mg (0.265 mmol) of oily brown Salsolidine in a yield of 100%. The resulting Salsolidine was then reacted with 2,3,4,6-tetra-O-acetyl-β-D-glucospyranosyl isothiocyanate (hereinafter abbreviated as GITC) in acetonitrile to obtain a diastereomer. The diastereomer was analyzed by high performance liquid chromatography (column: Develosil ODS-5, manufactured by Nomura Kagaku K.K., eluent: acetonitrile/water=3:4 by volume, buffer: ammonium phosphate) to find that Salsolidine obtained has an optical purity of 95%. Therefore, the optical purity of the N-acetylsalsolidine obtained by asymmetric hydrogenation was also 95%ee.

EXAMPLE 4

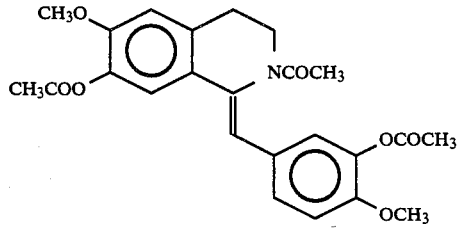

-continued

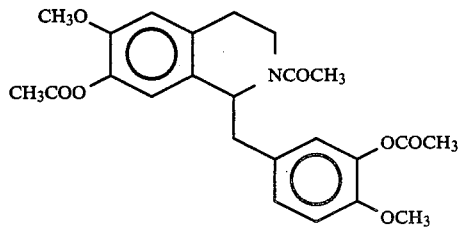

In a dried Schlenk-tube having its atmosphere displaced with argon, 118.6 mg (0.270 mmol) of (Z)-N-acetyl-7-acetoxy-1-(3-acetoxy-4-methoxyphenylmethylene)-6-methoxy-1,2,3,4-tetrahydroisoquinoline was charged and dissolved in 1.5 ml of methylene chloride. To the solution was further added 7.5 ml of ethanol, followed by degasification by freezing three times. Separately, in a dried Schlenk-tube having its atmosphere displaced with argon, 1.1 mg ($6.5 \times 10^{-4}$ mmol) of $Ru_2Cl_4((R)-(+)-BINAP)_2N(C_2H_5)_3$ was charged and dissolved in 1.5 ml of methylene chloride which had been previously degassed by freezing three times. To the solution was further added 7.5 ml of ethanol. Both the solutions were transferred to a pressure bottle and subjected to hydrogenation under a hydrogen pressure of 4 atms. at 23° C. for 62 hours while stirring. After completion of the reaction, the solvent was removed by distillation under reduced pressure, and the residue was purified by silica gel column chromatography (silica gel: 15 g, eluent: ethyl acetate/hexane=3:1 by volume) to give 104.7 mg (0.237 mmol) of (R)-N-acetyl-7-acetoxy-1-(3-acetoxy-4-methoxyphenylmethyl)-6-methoxy-1,2,3,4-tetrahydroisoquinoline (hereinafter referred to as acetylated N-acetylnorreticurine) in a yield of 88%.

The resulting acetylated N-acetylnorleticurine was deacylated in the same manner as in Example 3 to obtain Norleticurine which was then reacted with GITC in acetonitrile to form a diastereomer. High performance liquid chromatography of the diastereomer revealed that the N-acetyl-7-acetoxy-1-(3-acetoxy-4-methoxyphenoxymethyl)-6-methoxy-1,2,3,4-tetrahydroisoquinoline obtained by the asymmetric hydrogenation had an optical purity of 96%ee.

EXAMPLE 5

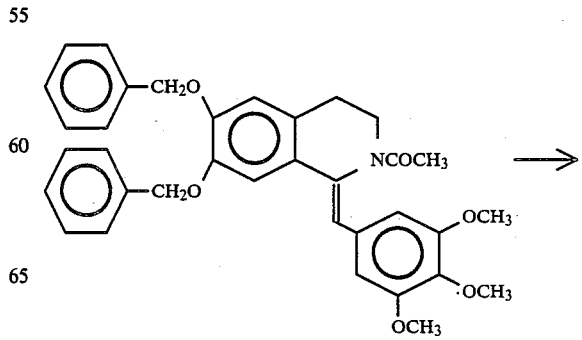

-continued

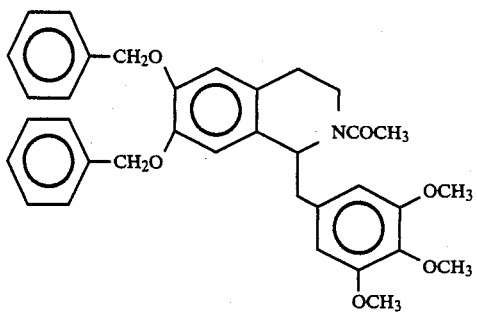

In 1.5 ml of methylene chloride was dissolved 100.8 mg (0.178 mmol) of (Z)-N-acetyl-6,7-dibenzyloxy-1-(3,4,5-trimethoxyphenylmethylene)-1,2,3,4-tetrahydroisoquinoline, and 7.5 ml of ethanol was further added thereto. A separately prepared solution of 2.9 mg ($1.7 \times 10^{-3}$ mmol) of $Ru_2Cl_4((S)\text{-}(-)\text{-}BINAP)_2N(C_2H_5)_3$ in 1.5 ml of methylene chloride was added to the above prepared solution, and the mixture was transferred to an autoclave. The mixture was subjected to hydrogenation at 23° C. for 62 hours at a hydrogen pressure of 4 kg/cm² while stirring. After completion of the reaction, the solvent was removed by distillation, and the residue was purified by silica gel column chromatography (silica gel: 15 g, eluent: ethyl acetate/hexane=3:1 by volume) to give 92.8 mg (0.164 mmol) of (S)-N-acetyl-6,7-dibenzyloxy-1-(3,4,5-trimethoxyphenylmethyl)-1,2,3,4-tetrahydroisoquinoline in a yield of 92%. The optical rotation $[\alpha]_D^{24}$ of this product was +62.8° (c=0.92, $CHCl_3$).

A mixture consisting of 21.5 mg (0.038 mmol) of the thus obtained hydrogenation product, 100 mg (1.52 mmol) of 85% potassium hydroxide, 0.05 ml (0.8 mmol) of 80% hydrazine hydrate, and 2 ml of ethylene glycol was allowed to react at 180° C. for 14 hours under an argon stream. To the reaction mixture was added 15 ml of 1N hydrochloric acid, and the mixture was washed three times with 10 ml portions of methylene chloride. To the aqueous layer was added 10 ml of a 2N sodium hydroxide aqueous solution to make it alkaline, and the solution was extracted three times with 10 ml portions of methylene chloride. The extract was dried over anhydrous sodium sulfate, and the methylene chloride was removed therefrom by distillation to obtain (S)-(−)-6,7-dibenzyloxy-1-(3,4,5-trimethoxyphenylmethyl)-1,2,3,4-tetrahydroisoquinoline as a brown oil. The resulting isoquinoline was reacted with GITC to form a diastereomer which was then analyzed by high performance liquid chromatography to find that the (S)-N-acetyl-6,7-dibenzyloxy-1-(3,4,5-trimethoxyphenylmethyl)-1,2,3,4-tetrahydroisoquinoline resulted from the asymmetric hydrogenation had an optical purity of 99.5%ee.

EXAMPLE 6

The same procedure of Example 1 was repeated except for using $Ru((R)\text{-}(+)\text{-}BINAP)(O_2CCH_3)_2$ as a catalyst to obtain (R)-N-acetyltetrahydropapaverine in a yield of 100% and an optical yield of 99.5%.

EXAMPLE 7

The same procedure of Example 1 was repeated except for using $Ru_2Cl_4((R)\text{-}(+)\text{-}p\text{-}Tol\ BINAP)_2N(C_2H_5)_3$ as a catalyst to obtain (R)-N-acetyltetrahydropapaverine in a yield of 90% and an optical yield of 98%.

EXAMPLE 8

The same procedure of Example 1 was repeated except for using $Ru_2Cl_4((R)\text{-}(+)\text{-}p\text{-}t\text{-}butyl\ BINAP)_2N(C_2H_5)_3$ as a catalyst to obtain (R)-N-acetyltetrahydropapaverine in a yield of 80% and an optical yield of 95%.

EXAMPLE 9

The same procedure of Example 1 was repeated except for using $Ru((R)\text{-}(+)\text{-}p\text{-}Tol\ BINAP)(O_2CCF_3)_2$ as a catalyst to obtain (R)-N-acetyltetrahydropapaverine in a yield of 95% and an optical yield of 97%.

EXAMPLE 10

In a dried Schlenk-tube having its atmosphere displaced with argon, 194.6 mg (0.527 mmol) of (Z)-N-formyl-6,7-dimethoxy-1-(3,4-dimethoxyphenylmethylene)-1,2,3,4-tetrahydroisoquinoline was charged and dissolved in 3 ml of methylene chloride. To the solution was further added 10 ml of ethanol, followed by degasification by freezing three times. Separately, in a dried Schlenk-tube having its atmosphere displaced with argon, 4.0 mg ($4.75 \times 10^{-3}$ mmol) of $Ru((R)\text{-}(+)\text{-}BINAP)\text{-}(O_2CCH_3)_2$ was charged and dissolved in 5 ml of ethanol which had been previously degassed by freezing three times. Both the solutions were transferred to an autoclave and stirred at 24° C. for 24 hours and then at 25° to 30° C. for 48 hours at a hydrogen pressure of 4 kg/cm² to effect hydrogenation. After completion of the reaction, the solvent was removed by distillation, and the residue was purified by silica gel column chromatography (silica gel: 20 g, eluent: ethyl acetate/hexane=3:1 by volume) to obtain 176.9 mg (0.477 mmol) of (R)-(−)-N-formyltetrahydropapaverine as white needle-like crystals in a yield of 91%.

To 42.1 mg (0.113 mmol) of the resulting (R)-(−)-N-formyltetrahydropapaverine were added 6 ml of ethanol and 4 ml of a 2N sodium hydroxide aqueous solution in an argon stream, followed by stirring at 80° C. for 12 hours. After completion of the reaction, 10 ml of water was added to the reaction mixture, and the aqueous solution was saturated with sodium chloride and then extracted three times with 10 ml portions of methylene chloride. The extract was dried over anhydrous sodium sulfate, and the solvent was removed from the residue by distillation under reduced pressure to obtain 38.3 mg (0.112 mmol) of (R)-(+)-tetrahydropapaverine as a brown oil in a yield of 99%. One milligram of this product was reacted with GITC in 0.2 ml of acetonitrile, and the resulting diastereomer was analyzed by high performance liquid chromatography to find that the optical yield was 97.6%.

EXAMPLE 11

The same procedure of Example 10 was repeated except for using 204.9 mg (0.555 mmol) of (Z)-N-formyl-6,7-dimethoxy-1-(3,4-dimethoxyphenylmethylene)-1,2,3,4-tetrahydroquinoline as a substrate and 5.1 mg ($6.06 \times 10^{-3}$ mmol) of $Ru((S)\text{-}(-)\text{-}BINAP)(O_2CCH_3)_2$ as a catalyst. As a result, 219.0 mg (0.555 mmol) (yield: 100%) of (S)-(+)-N-formyltetrahydropapaverine was obtained as white needle-like crystals.

The resulting hydrogenation product weighing 25.4 mg (0.0685 mmol) was subjected to deformylation with a 2N sodium hydroxide aqueous solution in the same manner as in Example 10 to obtain 33.1 mg (0.0685 mmol) (yield: 100%) of (S)-(—)-tetrahydropapaverine as a brown oil. Analysis of a diastereomer formed by the reaction with GITC proved that the optical yield was 100%.

According to the process of the present invention, N-acyltetrahydroisoquinolines useful as intermediates for isoquinoline type alkaloids can be synthesized efficiently in the form of a pure optical isomer useful for the purpose without involving optical resolution of a racemate. Therefore, the process of this invention provides great industrial advantages.

While the invention has been described in detail and with reference to specific embodiments thereof, it will be apparent to one skilled in the art that various changes and modifications can be made therein without departing from the spirit and scope thereof.

What is claimed is:

1. A process for preparing an N-acyltetrahydroiso quinoline represented by formula (II)

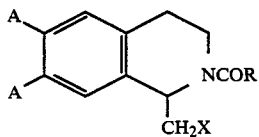
(II)

wherein A represents a hydroxyl group, a lower alkoxy group, an acetoxy group, or a benzyloxy group; R represents a hydrogen atom, a lower alkyl group, or a phenyl group; and X represents a hydrogen atom, a phenyl group, or a phenyl group substituted with a hydroxyl group, a lower alkoxy group, or an acetoxy group, which comprises asymmetrically hydrogenating an N-acyl-1-methylenetetrahydroisoquinoline or N-acyl-1-benzylidenetetrahydroiso quinoline represented by formula (I)

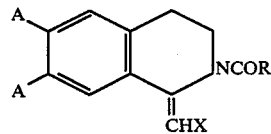
(I)

wherein A, R, and X are as defined above, in the presence of an optically active ruthenium-phosphine complex as a catalyst selected from $Ru(BINAP)(O_2CCH_3)_2$, $Ru(p\text{-}Tol\ BINAP)_2(O_2CCH_3)_2$, $Ru(BINAP)(O_2Ct\text{-}Bu)_2$,

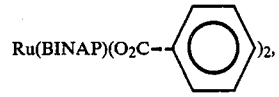

$Ru(p\text{-}Tol\ BINAP)(O_2CCH_3)_2$, $Ru(p\text{-}Tol\ BINAP)\text{-}(O_2CCF_3)_2$, $Ru(p\text{-}t\text{-}Bu\ BINAP)(O_2CCH_3)_2$, $Ru(5\text{-}acetylamino\ BINAP)(O_2CCH_3)_2$, $Ru(BINAP)$, or

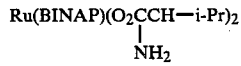

wherein BINAP represents 2,2'-bis(diphenylphosphino)-1,1'-binaphthyl; p-Tol BINAP represents 2,2'-bis(di-p-tolylphosphino)-1,1'-binaphthyl; p-t-Bu BINAP represents 2,2'-bis(di-p-t-butylphenylphosphino-1,1'-binaphthyl; 5-acetylamino BINAP represents 2,2'-bis(di-phenylphosphino)-5,5'-diacetylamino-1,1'-binaphthyl; and i-Pr represents an isopropyl group.

2. A process as in claim 1, wherein said optically active ruthenium-phosphine complex is $Ru(BINAP)\text{-}(O_2CCH_3)_2$.

3. A process as in claim 1, wherein said optically active ruthenium-phosphine complex is $Ru(p\text{-}Tol\ BINAP)_2(O_2CCH_3)_2$.

4. A process as in claim 1, wherein said optically active ruthenium-phosphine complex is $Ru(p\text{-}Tol\ BINAP)(O_2CCH_3)_2$.

5. A process as in claim 1, wherein said optically active ruthenium-phosphine complex is $Ru(p\text{-}Tol\ BINAP)(O_2CCF_3)_2$.

6. A process as in claim 1, wherein said optically active ruthenium-phosphine complex is $Ru(p\text{-}t\text{-}Bu\ BINAP)(O_2CCH_3)_2$.

* * * * *

UNITED STATES PATENT AND TRADEMARK OFFICE
CERTIFICATE OF CORRECTION

PATENT NO. : 4,851,537
DATED     : 7/25/89
INVENTOR(S) : Ryoji Noyori

It is certified that error appears in the above-identified patent and that said Letters Patent is hereby corrected as shown below:

Column 4, lines 58-60, change

"Ru(BINAP)(O$_2$CCH-i-Pr)$_2$" to --Ru(BINAP)(O$_2$CCH-i-Pr)$_2$--.
$\quad\quad\quad\quad\quad\;$ |  $\quad\quad\quad\quad\quad\quad\quad\quad\quad\;$ |
$\quad\quad\quad\quad\quad$ NH$_2$ $\quad\quad\quad\quad\quad\quad\quad\quad\;$ NH$_2$ Claim 1, lines 25-27 (Column 12, lines 25-27), change "Ru(BINAP)(O$_2$CCH-i-Pr)$_2$" to --Ru(BINAP)(O$_2$CCH-i-Pr)$_2$--.
$\quad\quad\quad\quad\quad\;$ |  $\quad\quad\quad\quad\quad\quad\quad\quad\quad\;$ |
$\quad\quad\quad\quad\quad$ NH$_2$ $\quad\quad\quad\quad\quad\quad\quad\quad\;$ NH$_2$ Signed and Sealed this Ninth Day of November, 1993

Attest:

BRUCE LEHMAN

*Attesting Officer*  *Commissioner of Patents and Trademarks*